United States Patent [19]

Grant

[11] Patent Number: 5,018,534
[45] Date of Patent: May 28, 1991

[54] INTRAVENOUS CATHETER SHIELD AND RETAINER

[76] Inventor: Michael L. Grant, P.O. Box 95744, Oklahoma City, Okla. 73143

[21] Appl. No.: 490,904

[22] Filed: Mar. 9, 1990

Related U.S. Application Data

[63] Continuation-in-part of Ser. No. 378,359, Jun. 26, 1989, Pat. No. 4,919,150.

[51] Int. Cl.$^5$ .......................... A61F 5/37; A61F 13/00
[52] U.S. Cl. ..................................... 128/877; 128/888; 128/DIG. 6
[58] Field of Search ......... 128/877, 888, 887, DIG. 6, 128/DIG. 26, 87 R, 869, 889

[56] References Cited

U.S. PATENT DOCUMENTS

| | | | |
|---|---|---|---|
| 3,722,508 | 3/1973 | Roberts | 128/877 |
| 3,782,378 | 1/1974 | Page | 128/888 |
| 3,900,026 | 8/1975 | Wagner | 128/881 |
| 4,161,261 | 7/1979 | Frater | 220/337 |
| 4,316,461 | 2/1982 | Marais et al. | 604/179 |
| 4,505,270 | 3/1985 | Miles | 128/877 X |
| 4,517,971 | 5/1985 | Sorbonne | 128/879 |
| 4,576,589 | 3/1986 | Kraus et al. | 604/8 |
| 4,649,907 | 3/1987 | Whitehead et al. | 128/84 C |
| 4,870,976 | 10/1989 | Denny | 128/877 |

FOREIGN PATENT DOCUMENTS 0266176 10/1987 European Pat. Off. ............ 128/877

Primary Examiner—Robert A. Hafer
Assistant Examiner—Michael Brown
Attorney, Agent, or Firm—Robert K. Rhea

[57] ABSTRACT

An intravenous catheter shield is formed by a base underlying a portion of the patient's limb containing an infusion needle. A transparent channel-like housing in higedly connected with the base and overlies the catheter area in vertical spaced relation. Velcro equipped straps secure the patient's limb to the base and the surface of the base is longitudinally provided with recesses in resilient mateiral which grip an IV tube extending into the housing and connected with a catheter.

4 Claims, 3 Drawing Sheets

INTRAVENOUS CATHETER SHIELD AND RETAINER

CROSS REFERENCE TO RELATED APPLICATION

This application is a continuation-in-part of an application filed by me in the United States Patent and Trademark Office on June 26, 1989, under Ser. No. 07/378,359 for Intravenous Catheter Shield and Retainer, now U.S. Pat. No. 4,919,150.

BACKGROUND OF THE INVENTION

1. Field of the invention

The present invention relates to the field of intravenous catheters and more particularly to a guard or shield for the venipuncture site, a catheter and an intravenous tubing retainer.

When intravenous fluid is to be periodically injected into a patient over an extended time period, it has been the general practice to insert a cannula beneath the surface of the skin into a vein and to retain the cannula in position by adhesive tape. This simple arrangement is effective; however, problems can arise in that the adhesive tape sometimes prevents visual inspection of the puncture site and often provides inadequate retention of the cannula as the patient moves or as the nurse inserts a needle to inject other medication.

Further, the adhesive tape is irritating particularly when the patient is sensitive to the adhesive tape, which causes irritation and creates considerable discomfort for the patient at the area of the intravenous catheter.

2. Description of the prior art

Prior patents generally disclose a base member, which may be planar in general configuration, and supports a section of intravenous tubing connected with a catheter and is attached to the arm or leg of the patient by encircling straps.

These devices, are generally satisfactory, but have the disadvantage when used with an active patient, such as a child, they do not provide adequate support for either the tubing or the catheter. One present method of protecting the needle site is the use of a styrofoam cup, severed in half, with the base portion inverted and taped over the needle area or catheter with cloth tape. This sometimes causes the needle to come out, after extended use, such as three or more days, and the skin to become raw. The cloth tape, as stated above, irritates the skin and must be removed to inspect the condition of the patient's vein.

U.S. Pat. No. 3,722,508 discloses an infusion guard and immobilizer for intravenous infusions. This device comprises a U-shaped channel portion underlying a patient's arm and a rigid, inverted U-shaped bridge spanning and removably secured to the upstanding edges of the U-shaped channel. The bridge also supports intravenous tubing and the entire unit is secured to a patient's limb by Velcro hook and eye straps.

U.S. Pat. No. 4,517,971 discloses a guard for a venipuncture site which comprises a base member taped to a patient's limb which supports the intravenous needle or catheter and includes a lid portion hingedly connected at one end to one end portion of the base for movement toward and away from the base in shielding relation with respect to the catheter position.

U.S. Pat. No. 3,900,026 discloses an intravenous needle stabilizing device which comprises a generally rectangular downwardly open cup-like shield having flanged edges projecting laterally which are employed to secure the device to a patient's limb. One portion of the cup-like shield provides gripping members for supporting a catheter when inserted into the vein of the patient to prevent movement of the catheter.

U.S. Pat. No. 4,316,461 discloses a vascular stabilizer comprising a rectangular base having a major medical longitudinal aperture or slot which straddles a vein of the patient when placed thereover and includes an insertion slot extending through the base which stabilizes the catheter when inserted into the patient's vein. The base being attached to the patient's limb by strap members.

U.S. Pat. No. 3,782,378 discloses a shield for an intravenous catheter which is formed by a doughnut-like annulus formed from soft resilient material having a stiffening ring extending around its toric axis for securing a pair of bands thereto and encircling the patient's limb over the position of a catheter site. A pair of resilient strips are diametrically crossed and span the distance between the periphery of the ring at 90° positions for overlying a catheter when the annulus is centrally placed over the catheter position. A transparent cover sealed with the annulus spans the central opening and permits visual observation of the catheter when the shield is in place.

European Patent Application No. 0 266 176 discloses a shield for protecting an intravenous needle formed by a generally rectangular base utilizing strap members for securing the base to a patient's limb and an inverted open channel-like housing overlying the base. The housing is releasably secured to the base and supports intravenous tubing leading to a needle underlying the top of the base within the housing area.

U.S. Pat. No. 4,576,589 discloses a catheter drainage apparatus which features a tubing gripping spring clamp.

U.S. Pat. No. 4,161,261 discloses hingedly connecting a lid to another member by a series of interdigitated hinge members having a central hinged pin.

This invention is distinctive over the above described devices by providing a base which supports a portion of the patient's arm or leg by being attached thereto, in underlying relation, by strap members. A transparent housing, removably connected with the base, shields the catheter or intravenous tubular connection or puncture site of the patient's vein.

The base also supports the adjacent end portion of the intravenous tubing to prevent movement of the tubing, particularly at its end portion connected with the catheter.

SUMMARY OF THE INVENTION

An elongated rigid board-like member of selected length and width underlies a section of the patient's arm and is attached thereto as by hook and eye Velcro equipped straps extending transversely across the patient's limb and connected with opposing side portions of the base member.

An inverted U-shaped in cross section member, spans the patient's arm and hand in longitudinal relation, with side edge portions of the housing removably attached to respective side edge portions of the base member. At least one, preferably both ends of the housing allow the intravenous tubing to enter the housing, above the patient's arm or hand and be connected with a previously installed catheter. The tubing extending out of the housing longitudinally thereof and frictionally secured to the exterior of the housing or base.

The principal object of this invention is to provide a transparent shield for a catheter and a retainer for intravenous tubing, which permits visual inspection of the catheter site, without disassembling or removing any covering, such as tape or other material concealing the catheter or easily separating the housing from the base which will prevent movement of the intravenous tubing relative to the catheter, thus insuring a relatively long useful life of the vein puncturing position of the catheter.

DESCRIPTION OF THE PREFERRED EMBODIMENTS

Figure 1:
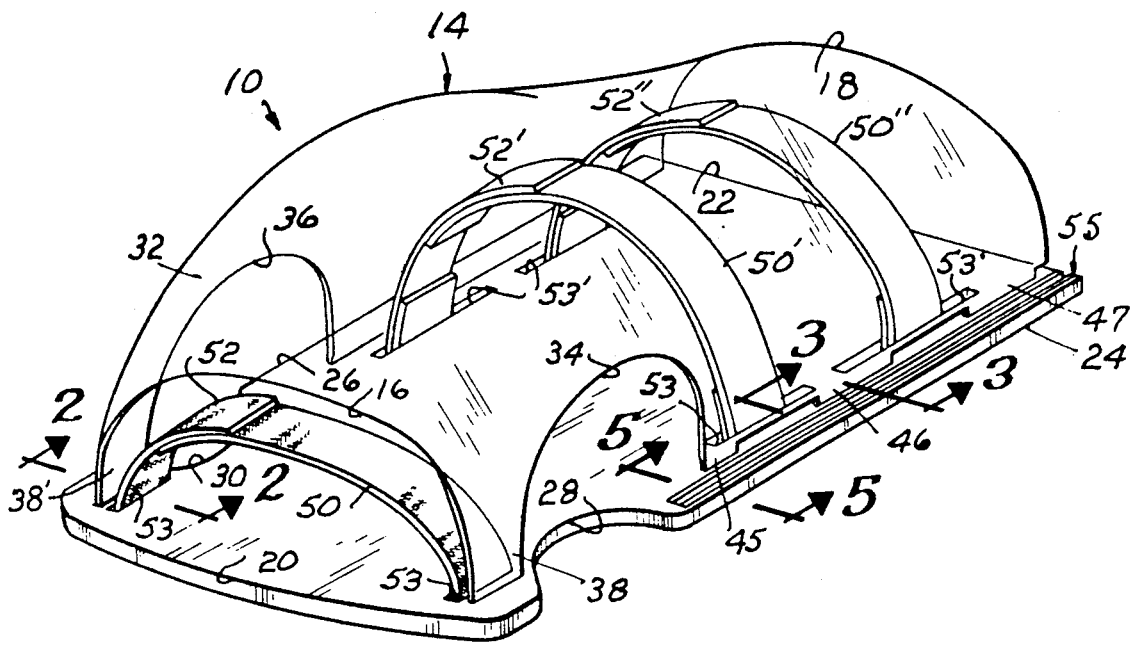
FIG. 1 is a perspective view of the device.

Like characters of reference designate like parts in those figures of the drawings in which they occur.

In the drawings:

Referring first to FIG. 1 reference numeral 10 indicates the device as a whole comprising an elongated, flat, rectangular base 12 and an overlying transparent housing 14 semitubular shaped transverse section. The transparent cover or housing 14 having an open forward end 16 and a rearward open end 18. The width of the base 12 and its thickness is selected in accordance with the range of sizes of the patients on which the device 10 is to be used and its length between its forward arcuate end 20 and its rearward end 22, normal to the respective sides 24 and 26, is substantially at least twice the width of the base. Adjacent its forward arcuate end 20, the respective sides 24 and 26 of the base are each provided with a substantially semicircular recess or indentation 28 and 30, respectively, for the purposes presently explained.

The forward upper surface of the housing 14 is arcuately curved downward and forwardly as at 32, so that the forward opening 16 of the substantially semitubular tubular housing 14 is adjacent but spaced above the upper surface of the base 12 providing sufficient room for the fingers, not shown, of a patient to extend forwardly and overhang the base edge 20 when his forearm is placed on the base 12. Opposing forward side edges of the housing 14 are arcuately cut away in cooperative alignment with the base recesses 28 and 30 to form opposed dome-like openings 34 and 36 for the purpose of permitting a patient's right or left hand thumb portion to project through the respective dome opening 34 or 36, and be comfortably received in the respective semicircular opening 28 or 30.

Figure 2:
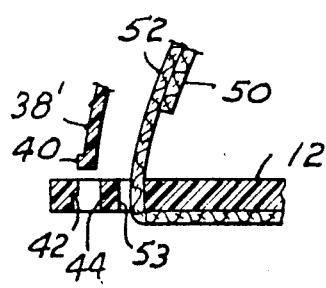
FIGS. 2 and 3 are vertical cross-sectional views, to a slightly larger scale, taken substantially along the lines 2—2 and 3—3, respectively, of FIG. 1.

The forward opening 16 and the respective lateral dome opening 34 and 36 of the housing define a hinge portion 38 at one side of the housing 14 for removably connecting it with the base. As illustrated by FIG. 2 each hinge connecting portion 38' is provided with a depending laterally projecting lug 40 which cooperatively engages a notch-like shoulder or hook 42 formed on the wall of a hinge member receiving opening 44 medially the thickness of the base 12. This permits manual pressure against the outward surface of the hinged portion 38 to disengage the lug 40 from the latch hook 42 and the housing to be hingedly pivoted laterally off the base. The side edges of the housing are inwardly disposed from the respective base side edges 24 and 26. Portions of the housing side edge opposite the hinge portion 38, as at 45, 46 and 47 are integrally joined, in a conventional plastic hinge forming manner, to the base 12 to permit the lateral pivoting movement of the housing off the base.

Figure 3:
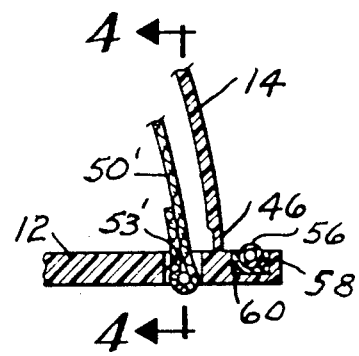
Figure 4:
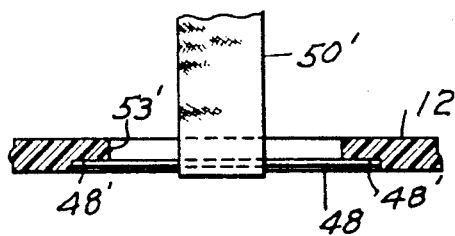
FIG. 4 is a vertical sectional view taken substantially along the line 4—4 of FIG. 3.
Figure 5:
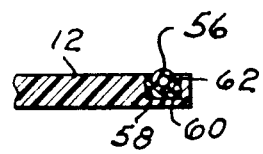
FIG. 5 is a vertical cross section to a larger scale taken substantially along the line 5—5 of FIG. 1.

The forward end portion of the base is attached to a patient's forearm or limb by fabric strap material having self adhering surfaces presently marketed under the trademark Velcro. This strap material forms a pair 50 and 52 with each strap connected at one end to the base bottom surface in any conventional manner, as by stapling, not shown, or by glue, or the like. As illustrated by FIG. 2 the Velcro strap 52 projects downwardly through an aperture 53 cooperatively formed in the base for the reception of one end portion of the Velcro strap 52. Similarly, the other Velcro strap 50 is connected through a base aperture 53' and is similarly secured to the bottom surface of the base. Obviously other fastening means may be used if desired or the straps may be one continuous strap with its end portions overlying the top surface of the base 12 as viewed in the drawings. A plurality of other pairs of Velcro strap members, preferably two 50'-52' and 50"-52" extend at their respective end portions, through loosely elongated base strap apertures or slots 53' and loosely surround, in doubled back upon themselves relation, an intermediate portion of a rod 48 (FIGS. 3 and 4). The rod 48 underlies the base 12 and projects at its respective end portions longitudinally beyond the respective slot 53' and is nested by cooperating base bottom surface, part-circular, recesses 48'. This permits longitudinal movement of the strap end portion relative to the respective slot 53' and rod 48 for the comfort of the patient.

Adjacent each of its lateral edges 24 and 26, the base is provided with a tubular raceway or tubeway 55, only one being shown, for retaining an intermediate portion of intravenous tubing 56 when inserted therein and having one end thereof attached to a cannula, not shown. The tubeway 55 comprises a recess 58 rectangular, in transverse cross-section, substantially coextensive with the respective base side 24 and 26 rearwardly of the thumb recesses 28 and 30. This recess 58 snugly receives and has bonded thereto an elongated, rectangular in cross section, length of plastic foam material 60 of a selected density centrally provided throughout its length with a part-circular recess 62 which frictionally grips and resiliently retains the tubing 56 therein when manually forced thereinto.

Figure 6:
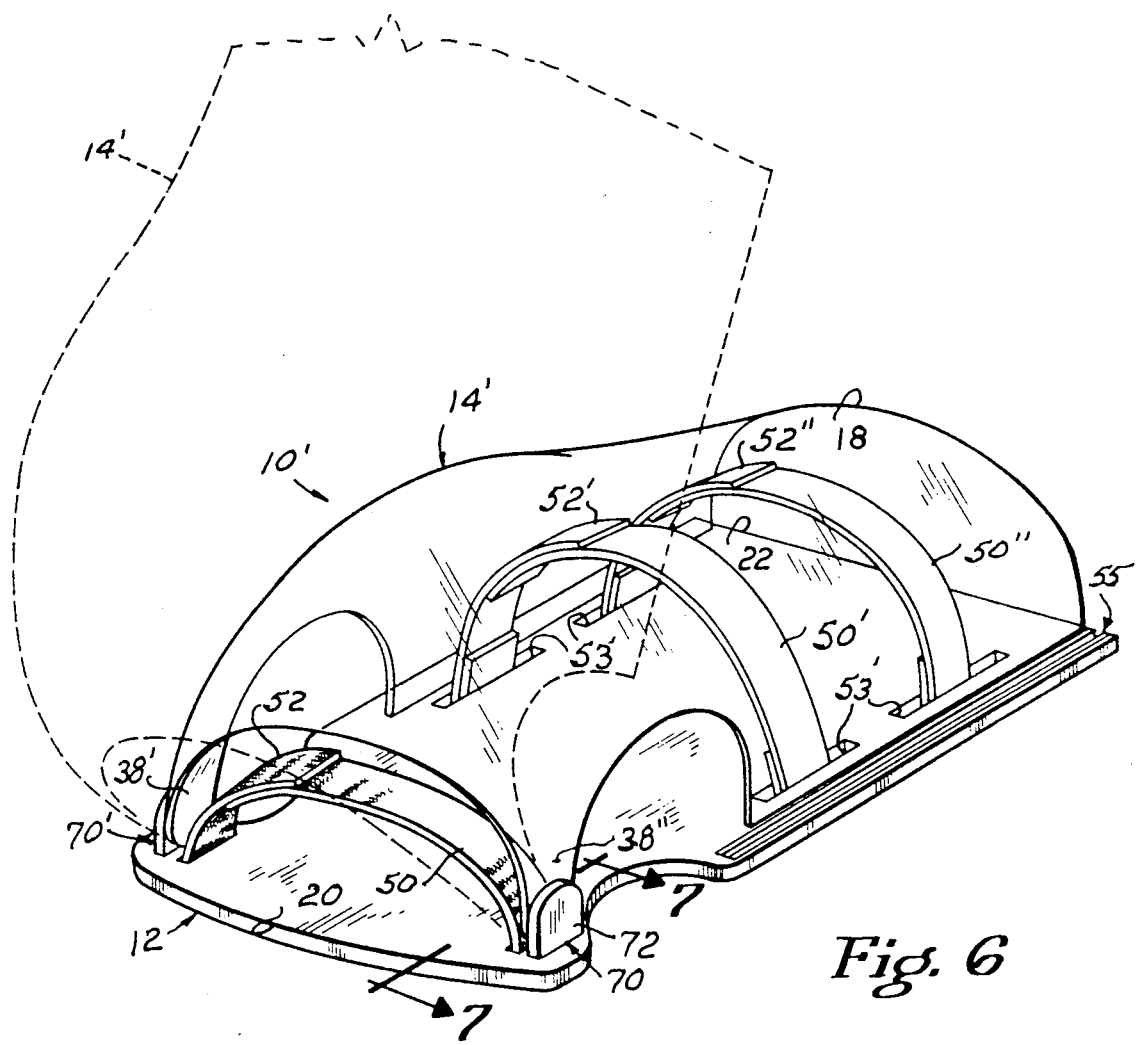
FIG. 6 is a perspective view similar to FIG. 1, illustrating an alternative hinge mounting of the housing on the base and illustrating a lifted position of the housing, by dotted lines.
Figure 7:
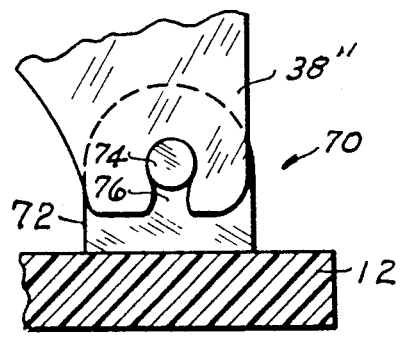
FIG. 7 is a horizontal sectional view to a larger scale, partially in elevation, taken substantially along the line 7—7 of FIG. 6, illustrating the manner of mounting the housing of FIG. 6 on its base.

Referring now to FIG. 6, a substantially identical embodiment of the device is illustrated at 10' in which identical parts bear identical reference numerals. The principal difference between the embodiment 10' and the embodiment of FIG. 1 is the hinge means 70 and 70' (FIG. 7) of the cover 14'. In this embodiment the forward end hinge portions 38' and 38" have been altered to permit the housing 14' to pivot about its forward end portion from a horizontal position on the base 12 to a substantially upright position, as illustrated by dotted lines.

The hinge means 70 comprises an upstanding part-circular projection 72 on the base adjacent the lateral outer surface of the housing hinge portion 38". In the interest of brevity only the hinge means 70 is described. A pin 74 projects horizontally inward from the inward surface of the projection 72 in upward spaced relation above the base top surface. The depending surface of the hinge portion 38' is provided with a downwardly open slot 76 pivotally straddling an intermediate portion of the pin 74 for vertical pivoting movement of the housing 14' about the axes of the pins 74.

Figure 8:
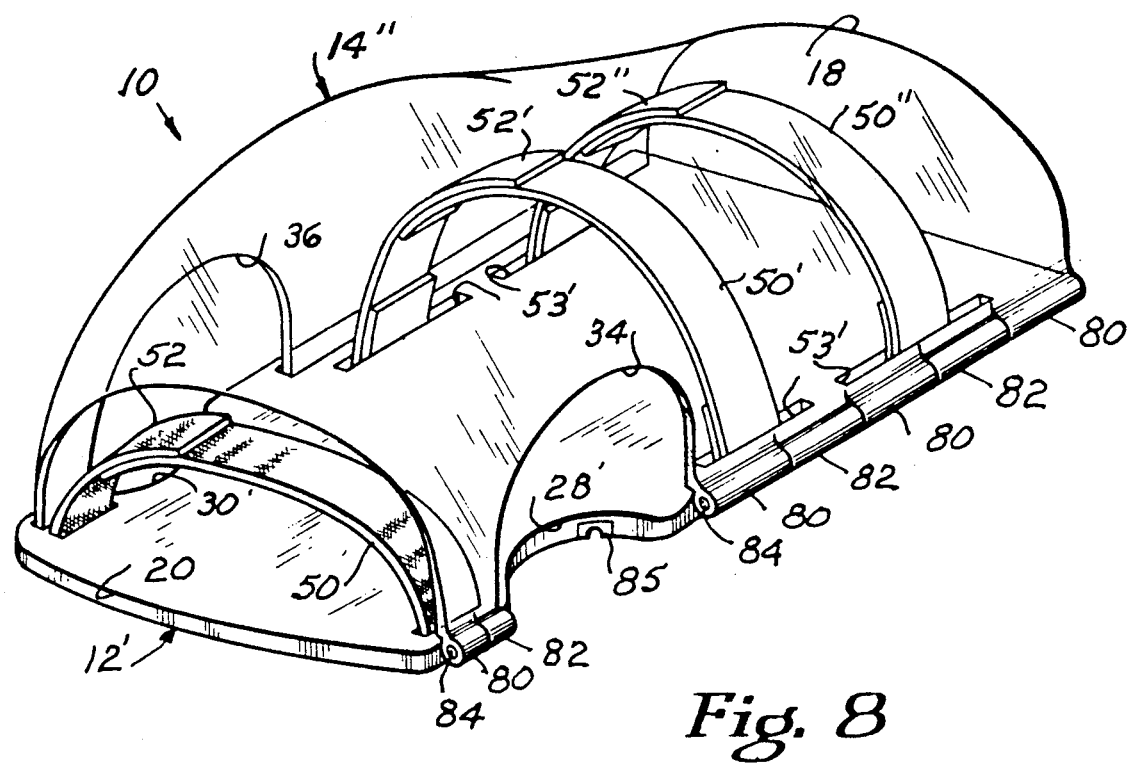
FIG. 8 is a perspective view, similar to FIG. 1, illustrating another manner of hingedly mounting the housing on the base; and, FIG. 9 is a bottom view, to a different scale, illustrating an alternative manner of mounting and holding intravenous tubing on the bottom surface of the base.
Figure 9:
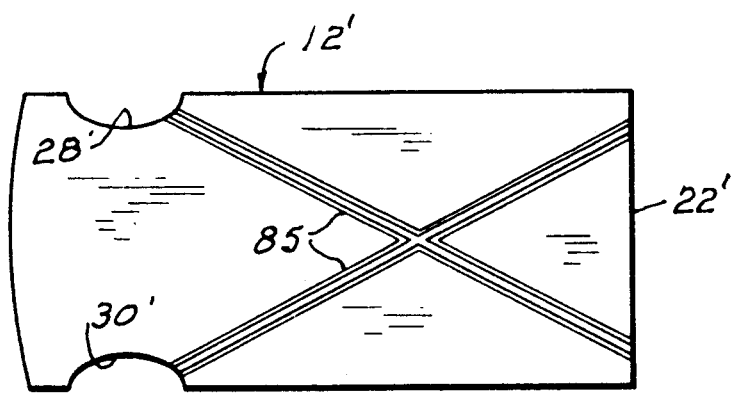

A further embodiment of the device indicated at 10" is illustrated by FIGS. 8 and 9 in which identical parts bear identical reference numerals and similar parts bear prime numerals. One longitudinal side edge of the base 12' in this embodiment is provided with a plurality of hinge members 80 which cooperatively receive hinge pin receiving members 82 depending from the respective sides of the cover 14". These hinge pin receiving members are disposed in interdigitated relation and respectively receive hinge pins 84. The opposite side of the housing is releasably connected with the base in the manner illustrated by FIG. 2 and described hereinabove. When the housing is in place on the base, these pins 84 may be manually removed for completely separating the housing from the base.

The bottom surface of the base 12' (FIG. 9) is provided with a crossed pattern of intravenous tube receiving recesses 85 which extend from the base rearward end 22' to the respective lateral thumb recess 28' and 30' so that the tubing 56, not shown, may be disposed in a selected straight or serpentine pattern for entering either side of the cover 14" at the recess openings 28' or 30'.

Obviously the invention is susceptible to changes or alterations without defeating its practicability. Therefore, I do not wish to be confined to the preferred embodiment shown in the drawings and described herein.

I claim:

1. A shield for protecting the position of an intravenous needle having one end of intravenous tubing connected thereto when the needle is inserted into a body part of a patient, comprising:
   an elongated generally planar base having opposing side edges for flatly underlying a portion of a patient's limb,
   said base having pairs of longitudinally spaced longitudinally elongated apertures adjacent its respective longitudinal marginal edges;
   a plurality of flexible strap means respectively extending through said plurality of base apertures for securing said base to the patient's limb;
   means for securing the respective strap of said strap means to the base for selectively positioning said respective strap intermediate the end limits of the respective elongated aperture,
   said strap securing means including an elongated rigid member underlying the base and longitudinally spanning the respective base aperture and secured at its respective end portions to the depending surface of said base;
   an elongated rigid transparent housing substantially inverted U-shape in transverse cross section having depending leg portions and an arcuate bight portion longitudinally overlying the base in laterally and vertically spaced relation with respect to the surface of the patient's limb and an intravenous needle location; and,
   hinge means pivotally securing housing leg hinge members to a side edge portion of said base for pivoting movement of the housing toward and away from said base,
   said hinge means including an upstanding projection on one end portion of said base adjacent its respective longitudinal side edge and adjacent the respective outer surface of said leg hinge members,
   each said leg hinge member having a depending edge surface and having a generally vertically disposed downwardly open slot in its depending edge; and,
   hinge pin means horizontally secured to said projection and projecting through the leg hinge member slots for vertical pivoting movement of the other end portion of said housing about a horizontal axis.

2. A shield for protecting the position of an intravenous needle having one end of intravenous tubing connected thereto when the needle is inserted into a body part of a patient, comprising:
   an elongated generally planar base having opposing side edges for flatly underlying a portion of a patient's limb, said base having pairs of longitudinally spaced longitudinally elongated apertures adjacent its respective longitudinal marginal edges;
   a plurality of flexible strap means respectively extending through said plurality of base apertures for securing said base to the patient's limb;
   means for securing the respective strap of said strap means to the base for selectively positioning said respective strap intermediate the end limits of the respective elongated aperture;
   an elongated rigid transparent housing substantially inverted U-shape in transverse cross section having depending leg portions and a arcuate bight portion longitudinally overlying the base in laterally and vertically spaced relation with respect to the surface of the patient's limb and an intravenous needle location; and,
   hinge means pivotally securing housing leg hinge members to a side edge portion of said base including an upstanding projection on one end portion of said base adjacent its respective longitudinal side edge and adjacent the respective outer surface of said leg hinge members,
   each said leg hinge member having a depending edge surface and having a generally vertically disposed downwardly open slot in its depending edge, and,
   hinge pin means horizontally secured to said projection and projecting through the leg hinge member slots for vertical pivoting movement of the other end portion of said housing about a horizontal axis.

3. The intravenous needle shield according to claim 2 in which said strap securing means includes:

an elongated rigid member underlying the base and longitudinally spanning the respective base aperture and secured at its respective end portions to the depending surface of said base.

4. The intravenous needle shield according to claim 3 in which one surface of said base is provided with a longitudinally extending groove and further including:

a coextensive length of resilient material filling the base groove, said resilient material having a coextensive part circular in cross recess in its outermost surface for resiliently retaining a length of intravenous tubing therein.

* * * * *